US011904176B1

(12) United States Patent
Sjoquist et al.

(10) Patent No.: US 11,904,176 B1
(45) Date of Patent: Feb. 20, 2024

(54) WEARABLE DEFIBRILLATOR SYSTEM FORWARDING PATIENT INFORMATION BASED ON RECIPIENT PROFILE AND/OR EVENT TYPE

(71) Applicant: West Affum Holdings DAC, Dublin (IE)

(72) Inventors: Steven E. Sjoquist, Lynnwood, WA (US); Jonathan P. Niegowski, Issaquah, WA (US); Zoie R. Engman, Kirkland, WA (US); Pamela F. Breske, Newcastle, WA (US)

(73) Assignee: West Affum Holdings DAC, Dublin (IE)

( * ) Notice: Subject to any disclaimer, the term of this patent is extended or adjusted under 35 U.S.C. 154(b) by 92 days.

(21) Appl. No.: 17/199,231

(22) Filed: Mar. 11, 2021

Related U.S. Application Data

(60) Provisional application No. 62/966,422, filed on Jan. 27, 2020.

(51) Int. Cl.
| *G16H 40/67* | (2018.01) |
| *A61N 1/39* | (2006.01) |
| *A61N 1/04* | (2006.01) |
| *A61N 1/02* | (2006.01) |

(52) U.S. Cl.
CPC .......... *A61N 1/3904* (2017.08); *A61N 1/025* (2013.01); *A61N 1/046* (2013.01); *A61N 1/0484* (2013.01); *G16H 40/67* (2018.01)

(58) Field of Classification Search
CPC ...... A61N 1/3904; A61N 1/025; A61N 1/046; A61N 1/0484; G16H 40/67
See application file for complete search history.

(56) References Cited

U.S. PATENT DOCUMENTS

| 3,724,355 A | 4/1973 | Busch et al. |
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |

(Continued)

FOREIGN PATENT DOCUMENTS

| DE | 2005060985 A2 | 6/2007 |
| EP | 2305110 A1 | 4/2011 |

(Continued)

OTHER PUBLICATIONS

Heartstart MRx and XL AED Algorithm—Application Note, Jul. 2001, Edition 2 Philips Healthcare, USA.

(Continued)

*Primary Examiner* — Ankit D Tejani
*Assistant Examiner* — Joshua Brendon Solomon
(74) *Attorney, Agent, or Firm* — Christensen O'Connor Johnson Kindness PLLC

(57) ABSTRACT

A WCD system is configured to monitor various characteristics of the WCD system including about the patient. The information collected by the WCD is generally referred to as "patient information." The WCD system is further configured to transmit certain of the patient information to different recipients based on predetermined profiles with which one or more of the recipients is associated. In various embodiments, different sets or subsets of the patient information may be sent to different recipients.

22 Claims, 9 Drawing Sheets

SAMPLE COMPONENTS OF WEARABLE CARDIOVERTER DEFIBRILLATOR (WCD) SYSTEM

(56) References Cited

U.S. PATENT DOCUMENTS

| | | |
|---|---|---|
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,753,759 B2 | 7/2010 | Pintor et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,047,648 B1 | 6/2015 | Lekutai et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Vollpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0282934 A1* | 9/2014 | Miasnik .......... H04W 4/90 726/5 |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0221645 A1 | 8/2018 | Medema et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |

(56) References Cited

U.S. PATENT DOCUMENTS

2019/0116896 A1    4/2019  Armour et al.
2019/0133445 A1*   5/2019  Eteminan .............. A61B 5/1112
2019/0321650 A1   10/2019  Raymond et al.

FOREIGN PATENT DOCUMENTS

| JP | 4320257 A | 3/2005 |
| JP | 5963767 A | 1/2014 |
| JP | 2014526282 A | 10/2014 |
| WO | 98/39061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

SAMPLE COMPONENTS OF WEARABLE CARDIOVERTER DEFIBRILLATOR (WCD) SYSTEM

*SAMPLE COMPONENTS OF EXTERNAL DEFIBRILLATOR*

*Sample Components of a WCD System With Profile-Based Notifications*

*General Communication Arrangement*

Example Server-Based Arrangement

FIG. 7 — *EXAMPLE RECIPIENT DEVICE WITH APP ARRANGEMENT*

801

820

| Event | Data |
|---|---|
| Medical | Patient parameters |
| Maint. | System parameters |
| General | Location, other |
| Patient | Custom events |
| Other | Various information |

Event Table

840

| Recipient | Profile | Contact |
|---|---|---|
| Medical | A, B, C | Contact |
| Family | B, C | Contact |
| EMS | A, C | Contact |
| Support | A, B, D | Contact |
| Other | A, B, C, D | Contact |

Profile Table

Notification Tables

FIG. 8

WEARABLE DEFIBRILLATOR SYSTEM FORWARDING PATIENT INFORMATION BASED ON RECIPIENT PROFILE AND/OR EVENT TYPE

CROSS REFERENCE TO RELATED PATENT APPLICATIONS

This patent application claims priority from U.S. Provisional Patent Application No. 62/966,422 filed on Jan. 27, 2020 entitled "WCD System Forwarding Event Information Based on Recipient Profile", the disclosure of which is hereby incorporated by reference for all purposes.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include individuals who have had a heart attack, or a prior SCA episode. A frequent recommendation is for these people to receive an Implantable Cardioverter Defibrillator ("ICD"). The ICD is surgically implanted in the chest, and continuously monitors the person's electrocardiogram ("ECG"). If certain types of heart arrhythmias are detected, then the ICD delivers an electric shock through the heart.

After being identified as having an increased risk of an SCA, and before receiving an ICD, these people are sometimes given a wearable cardioverter defibrillator ("WCD") system. A WCD system typically includes a harness, vest, or other garment for wearing by the patient. The system includes a defibrillator and external electrodes, which are attached on the inside of the harness, vest, or other garment. When a patient wears a WCD system, the external electrodes may then make good electrical contact with the patient's skin, and therefore can help monitor the patient's ECG. If a shockable heart arrhythmia is detected, then the defibrillator of the WCD system delivers the appropriate electric shock through the patient's body, and thus through the heart.

BRIEF SUMMARY

In accordance with aspects of this disclosure, a WCD system is configured to monitor various characteristics of the WCD including about the patient. The information collected by the WCD is generally referred to as "patient information." The WCD system is further configured to transmit certain elements of the patient information to different recipients based on predetermined profiles with which one or more of the recipients is associated. In various embodiments, different sets or subsets of the patient information may be sent to different recipients.

In certain embodiments, the particular sets or subsets of patient information transmitted to various recipients may be based on a type of event detected by the WCD system. For example, if a significant medical event is detected (e.g., ventricular tachycardia (VT), ventricular fibrillation (VF), or the like) certain patient information may be transmitted to medical personnel (e.g., the patient's medical professional or caregiver) while a different subset of the patient information may be transmitted to other interested individuals (e.g., family members or identified friends) or entities (e.g., Emergency Medical Services (EMS) or the like). In various embodiments, the events for which information is transmitted may include events detected by the WCD through monitoring, and may also or alternatively include events programmed by the patient or other user (e.g., input directly into the WCD or using a mobile device in communication with the WCD).

In various embodiments, the particular subset of Patient Information transmitted to a recipient depends on a profile with which the recipient is associated. For example, if the recipient is the patient's doctor, the WCD system may be configured to provide all or substantially all of the Patient Information associated with the event. Alternatively, if the recipient is a family member, the subset of Patient Information may include only information easily understood by non-medical personnel, such as the patient's location. In still another alternative, the subset of Patient Information may be tailored to assist a lay person to render aid such as by calling 911 or providing CPR, etc.

In various embodiments, the WCD system transmits the information as an electronic message (e.g., SMS or MMS message, RCS message, email message, instant message, or the like) to a mobile device (e.g., mobile phone or tablet) of the recipients. In other embodiments, the WCD system may make telephone calls to the recipients in which the notifications may be in the form of recorded or synthesized voice messages. In yet other embodiments, the WCD system may send information to a WCD system server, which in turn sends messages to the recipients, or email messages, or application notifications that the recipients receive via email or notification apps running on their computers, smartphones, laptops or other "connected" devices. In still other embodiments, the WCD system may send information to a computer-aided dispatch (CAD)-coupled server which then sends notifications to any of its users that may be in a position to render aid to the patient.

The foregoing brief summary is illustrative only and is not intended to be in any way limiting. In addition to the illustrative aspects, embodiments, and features described above, which need not all be present in all embodiments of the inventions disclosed herein, further aspects, embodiments, and features are set forth in the drawings and the following detailed description.

BRIEF DESCRIPTION OF THE DRAWINGS

FIG. 8 is a conceptual diagram illustrating notification tables that may be used in various implementations of the disclosure, according to embodiments.

DETAILED DESCRIPTION

A wearable cardioverter defibrillator (WCD) system made according to embodiments has several components. These components can be provided separately as modules that can be interconnected, or can be combined with other components, etc.

Figure 1:
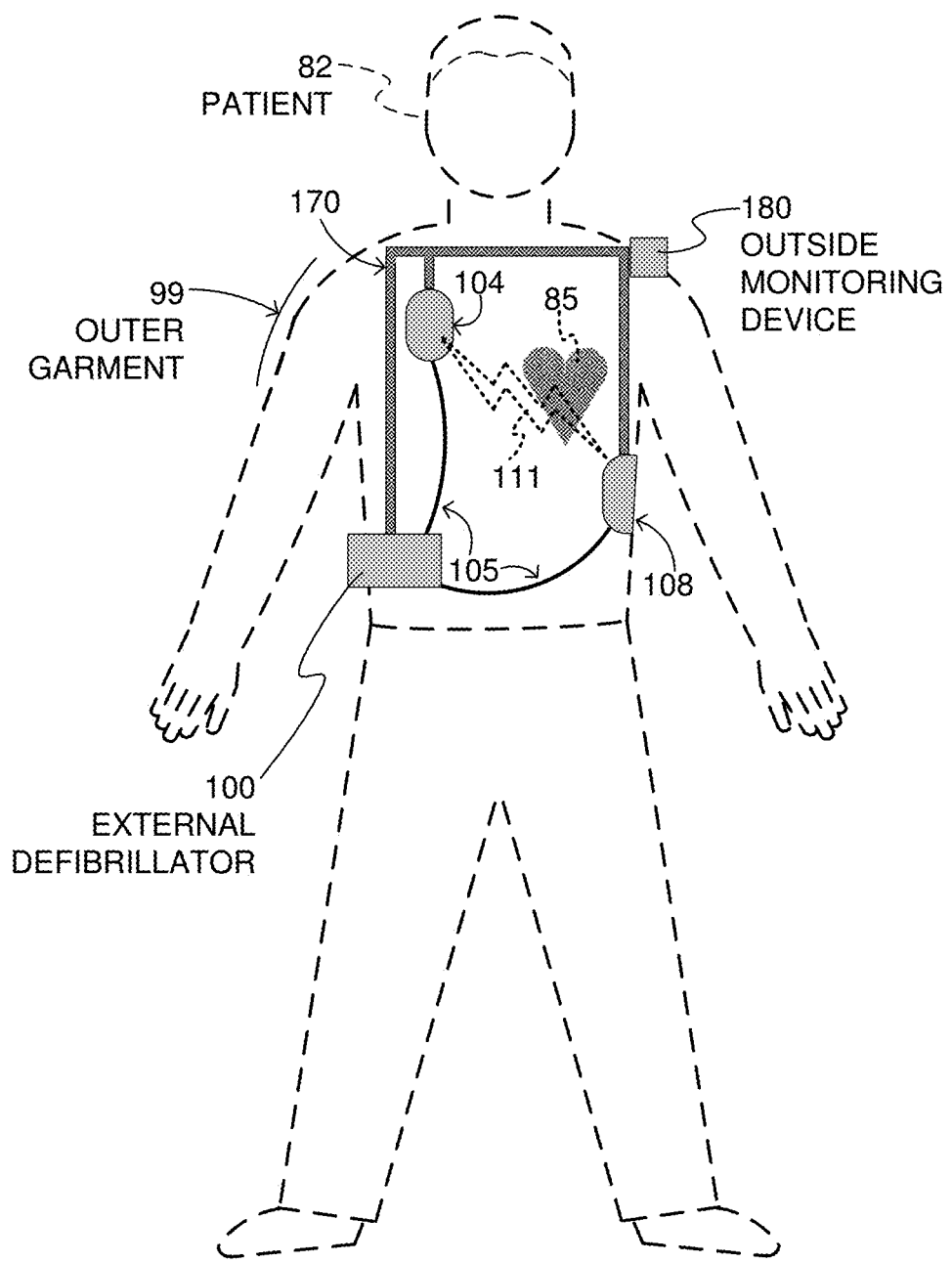
FIG. 1 is a diagram of components of a sample wearable cardioverter defibrillator (WCD) system, made according to embodiments.

FIG. 1 depicts a patient 82. Patient 82 may also be referred to as a person and/or wearer, since that patient wears components of the WCD system.

FIG. 1 also depicts components of a WCD system made according to embodiments. One such component is a support structure 170 that is wearable by patient 82. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways in different embodiments. For example, in one embodiment implemented in a single component or a combination of multiple components. In embodiments, support structure 170 could include a vest, a half-vest, a garment, etc. In such embodiments such items can be worn similarly to parallel articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient by adhesive material, for example as shown in U.S. Pat. No. 8,024,037. Support structure 170 can even be implemented as described for the support structure of US Pat. App. No. US 2017/0056682 A1, which is incorporated herein by reference. After review of this disclosure, in such embodiments, the person skilled in the art will recognize that additional components of the WCD system can be in the housing of a support structure instead of attached externally to the support structure, for example as described in the 2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as shock, defibrillation shock, therapy or therapy shock, is intended to go through and restart heart 85, in an effort to save the life of patient 82. Pulse 111 can further include one or more pacing pulses, and so on.

A defibrillator typically decides whether to defibrillate based on an ECG signal of the patient. However, some embodiments of external defibrillator 100 can initiate defibrillation (or hold-off defibrillation) based on a variety of inputs, with ECG merely being one of them.

Accordingly, in some embodiments of external defibrillator 100, signals such as physiological signals containing physiological data are obtained from patient 82. While the patient may be considered a "user" of the WCD system, in some embodiments, for example, a user of the WCD may also be a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers or sensors that are configured to render one or more physiological inputs from one or more patient parameters that it senses.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
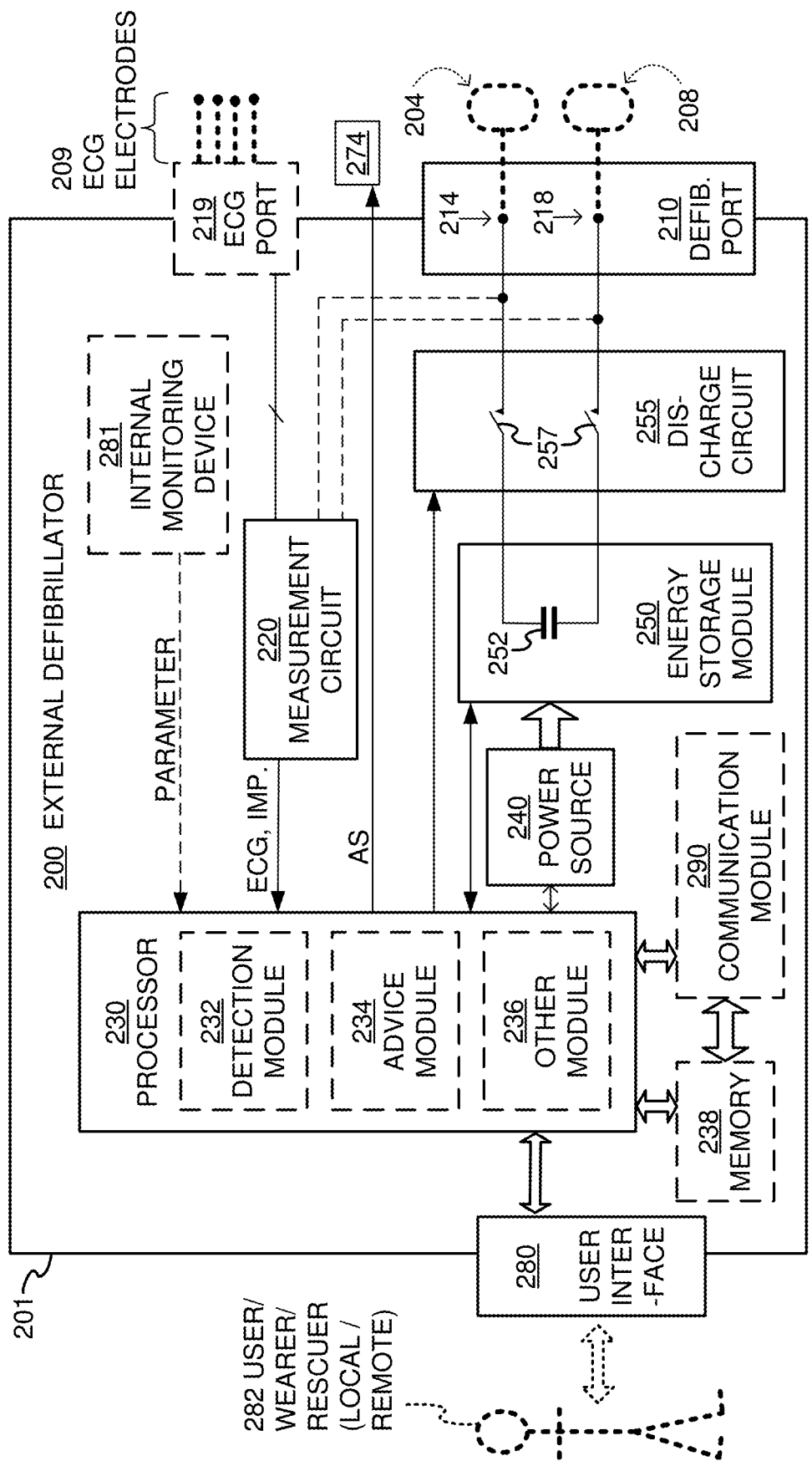
FIG. 2 is a diagram showing sample components of an external defibrillator, such as the one belonging in the WCD system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with the WCD system.

User interface 280 can be made in many ways according to various embodiments. User interface 280 may include output devices, which can be visual, audible or tactile, for communicating to a user by outputting images, sounds or vibrations. Images, sounds, vibrations, and anything that can be perceived by user 282 can also be called human perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which monitoring device can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a Doppler device for detecting blood flow, a cuff for detecting blood pressure, an optical sensor, illumination detectors and perhaps sources for detecting color change in tissue, a motion sensor, a device that can detect heart wall movement, a sound sensor, a device with a microphone, an SpO2 sensor, and so on. It will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2 or CO2; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer. In such cases, the patient parameter is a motion, one of the transducers may include a motion detector, and the physiological input is a motion measurement.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed if monitoring device 180 or 281 includes a GPS location sensor as per the above.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have an ECG port 219 in housing 201, for plugging in sensing electrodes 209, which are also known as ECG electrodes and ECG leads. It is also possible that sensing electrodes 209 can be connected continuously to ECG port 219, instead. Sensing electrodes 209 are types of transducers that can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Optionally, a WCD system according to embodiments also includes a fluid that it can deploy automatically between the electrodes and the patient's skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes 204, 208, and sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal AS from processor 230 that is described more fully later in this document.

In some embodiments, defibrillator 200 also includes a measurement circuit 220, as one or more of its sensors or transducers. Measurement circuit 220 senses one or more electrical physiological signals of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the physiological input reflects an ECG measurement. The parameter can be an ECG, which can be sensed as a voltage difference between electrodes 204, 208. In addition, the parameter can be an impedance, which can be sensed between electrodes 204, 208 and/or the connections of ECG port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module implemented using software includes a set of the instructions so as to offer or fulfill a particular functionality. Embodiments of modules and the functionality delivered are not limited by the embodiments described in this document.

Processor 230 can be considered to have one or more modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Various embodiments of processor 230 can include additional modules, such as other module 236, for other functions. In addition, if internal monitoring device 281 is indeed provided, it may be operated in part by processor 230, etc.

Embodiments of defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200 or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. Module 290 may also include such sub-components as may be deemed necessary by a person skilled in the art, for example an antenna, portions of a processor, supporting electronics, outlet for a telephone or a network cable, etc. This way, data, commands, etc. can be communicated. The data can include patient data, event information, therapy attempted, CPR performance, system data, environmental data, and so on. Defibrillator 200 in some embodiments can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

Figure 3:
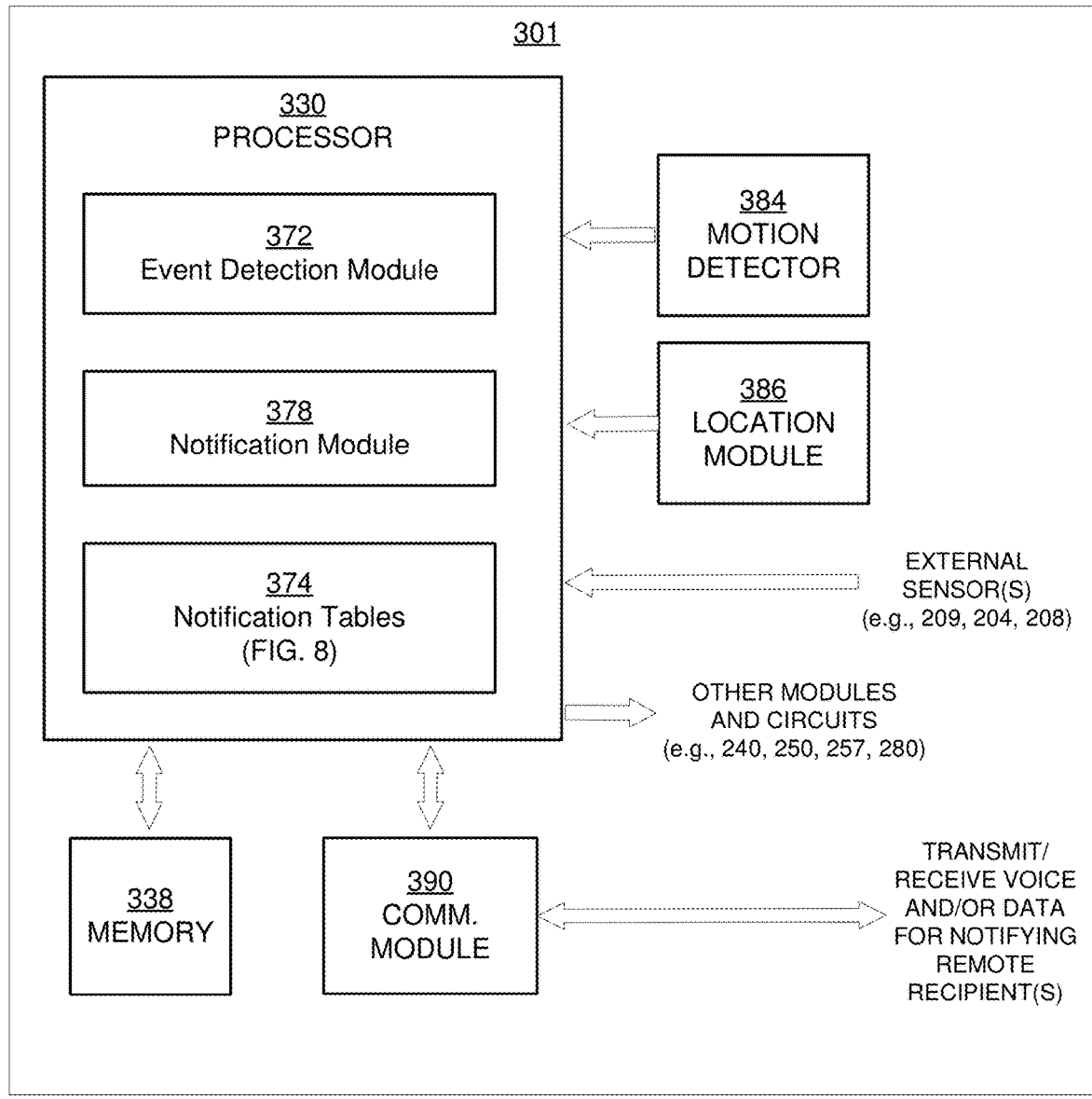
FIG. 3 is a diagram showing a collection of sample components of WCD systems for notifying remote responders, made according to embodiments.

FIG. 3 is a diagram showing sample components of an external defibrillator 301 similar to those of external defibrillator 200 of FIG. 2, in which some components are shown in more detail and some in less detail, according to embodiments. External defibrillator 301 can implemented in a WCD to deliver appropriate therapy (e.g., defibrillation shocks, cardioversion shocks, pacing, etc.) to a patient with an arrhythmia.

In embodiments, external defibrillator 301 includes a processor 330 coupled to a memory 338, a motion detector 384, a location module 386, and a communication module 390. Processor 330, memory 338, and communication module 390 are implemented in some embodiments as described above in conjunction with FIG. 2 for processor 230, memory 238, and communication module 290. Memory 338 can also be configured with patient ID information intended for inclusion in notifications that are described further below. External defibrillator 301, in embodiments, may also include other modules and components as shown in FIG. 2, but are omitted in FIG. 3 for simplicity of discussion.

In some embodiments, the components of external defibrillator 301 shown in FIG. 3 are disposed in a single housing or unit that is coupled to the support structure such as support structure 170 (FIG. 1). In other embodiments, one or more of these components are distributed over other parts of the WCD system. For example, in some embodiments, processor 330, location module 386 and communication module 390 are implemented at least in part using a mobile personal communication device such as a smartphone-like device as described below in conjunction with FIG. 5.

Motion detector 384, in some embodiments, is configured to detect motion of the patient, including patient motion due to having CPR performed on the patient. In embodiments, motion detector 384 is implemented using one or more of an accelerometer, force sensor, position sensor, transthoracic impedance sensors, etc. Some examples of position sensors include UWB position sensors, and magnetic field position sensors such as used in TrueCPR™ devices available from Physio-Control, Inc., Redmond, WA.

Location module 386, in some embodiments, is configured to determine the location of the patient. In some embodiments location module 386 determines the location of external defibrillator 301, other component of the WCD system, or possibly an accessory associated with the WCD system, to indicate the approximate location of the patient. Location module 386 in some embodiments uses one or more of GPS, cellular tower location, Wi-Fi access point locations, inertial navigation, etc. to determine the location of the patient. In embodiments of the WCD system having a mobile communication device (e.g., smartphone-like device), the location module may be incorporated into the mobile communication device and include an API to interface with a location service, such as Google Location Services.

In addition, in some embodiments processor 330 includes an event detection module 372, a notification module 378, and one or more notification tables 374. In some embodiments event detection module 372 and notification module 378 are implemented at least in part using software or programming stored in memory 338.

Event detection module 372 is configured to monitor the various sensors, inputs, and other circuits of the WCD system to identify a "notifiable event." For the purpose of this discussion, the term "notifiable event" refers to an event pertaining to the WCD system or to the patient for which a notification should be transmitted to one or more recipients. Many different occurrences may constitute a notifiable event. For example, the event detection module 372 may monitor the patient's physiological signals (via, e.g., measurement circuit 220) for the occurrence of a medical event (e.g., VT, VF, or other SCA), which would likely constitute a notifiable event. However, less urgent occurrences could also constitute notifiable events. For instance, system parameters may give rise to maintenance issues such as a low battery or other malfunction with the WCD system, which may give rise to notifiable events. In addition, notifiable events may be programmable by the patient or other person using the WCD, such as via user interface 280.

In accordance with this disclosure, different notifiable events may implicate different types of information. For example, the WCD system may experience only a minor maintenance issue, which could constitute a notifiable event since the proper operation of the WCD system is important to its effectiveness. In such an event, the patient's physiological data (e.g., ECG trace data) would be less relevant to the event. Alternatively, if the patient experiences a critical medical event (e.g., SCA), the WCD system maintenance data would likely be less relevant than the patient's physiological data. Accordingly, and as discussed in greater detail below, different notifiable events may have different patient information associated therewith.

Notification module 378 is configured to determine whether one or more other people or parties (also referred to as recipients in this context) should be notified, such as when event detection module 372 identifies that a notifiable event has occurred. In some embodiments, notification module 378 is configured to determine whether one or more other people or parties should be notified that the patient or the WCD has experienced some notifiable event.

In accordance with this disclosure, different recipients or, perhaps, classes of recipients may be dissimilarly situated regarding what information should be transmitted to such recipients. For example, a medical professional, such as the patient's doctor, could understand and make use of significantly more information about the patient's physiological data (e.g., the patient's ECG trace, blood oxygen levels, etc.) than could the patient's family members. Indeed, much of the information monitored by the WCD system would likely be unusable and even confusing to the typical lay person. Similarly, certain Emergency Medical Services (EMS) personnel would likely be most interested in certain patient information (e.g., the patient's vital signs and location) while other information may be less relevant (e.g., maintenance information about the WCD system). Accordingly, the notification module 378 may be configured to transmit different sets of patient information to different recipients or classes of recipients. For the purpose of this discussion, the term "patient information" refers to any data collected or detected by the WCD system about the patient or about the WCD system itself. Patient information may include, but is not limited to, patient state parameters, patient physiological data, system parameters, environmental parameters, and WCD maintenance data. Patient information may further include patient location information. In addition, patient information may include data about any medical events that the patient may be experiencing or may have experienced. Still further, patient information may include data about any therapy provided to or other actions performed on the patient. Other examples of patient information will become clear to those skilled in the art from a study of this disclosure.

Notification tables 374 may include sufficient information for the external defibrillator 301 to identify at least what patient information should be generated and/or reported in response to the occurrence of a notifiable event, and what set or subset of that patient information should be reported to various recipients either based on individual profiles associated with each recipient, or based on profiles associated with classes of recipients. For the purpose of this disclosure, the terms "recipients" and "classes of recipients" may be used interchangeably.

Turning briefly to FIG. 8, one example is shown of illustrative notification tables 801 that may be implemented in various embodiments. As noted above, different recipients may have need of different levels or categories of patient information. In addition, different notifiable events may have associated different types of patient information. Accordingly, notification tables 801 may be employed, in some embodiments, to specifically identify what patient information should be transmitted to which recipients, as is described more fully here.

Event table 820 is a data structure that identifies one or more specific (or types of) events for which patient information should be transmitted to recipients. In accordance with this disclosure, event table 820 may identify either specifically or by category the patient information that is implicated by each event. For example, event table 820 may generally identify medical events, maintenance events, device failures, equipment events, operational events, patient-specified events, and other types of events.

For example, a medical event may be identified as implicating patient physiological data as well as an estimate of the type of medical event being experienced by the patient (among other data). Medical events may further implicate a patient's therapy history; perhaps the patient's immediate therapy history (e.g., whether the patient has been shocked in connection with the current medical event, whether CPR was administered, or the like) as well as larger medical history (e.g., whether and what types of cardiac events the patient has previously experienced). However, the medical event may not implicate patient information such as a maintenance status of the WCD system. In contrast, a maintenance event may be identified as implicating such maintenance status (e.g., battery level, system diagnostic data, and the like). In addition to event-specific patient information, there may also be a category of general-purpose information that is always (or substantially always) implicated by notifiable events, such as the name of or other identifier for the patient and the patient's location.

In another example, operation analysis information may trigger a notifiable event to indicate that perhaps the patient is not properly trained or is having difficulty with the WCD, such as not wearing the WCD for enough hours in a typical day or over several days, perhaps the patient is experiencing an inordinate number of system alerts. Such information could trigger an operational event notification to indicate that the patient requires additional support with the WCD itself. In yet another example, information entered or provided by the patient to the WCD (e.g., through a mobile app associated with the WCD) such as patient symptoms, patient activity level, patient emotional state, reported overall patient condition, or the like, could trigger a notifiable event.

In this example, such information may be provided by the patient directly, such as through an interface of the WCD system or one of its accessories, or perhaps passively captured by the WCD system or one of its accessories. In one specific example, a mobile device executing a health app may passively collect activity information about the patient and provide such information to the WCD system or one of its accessories. Such collected patient activity information could be used to trigger a notifiable event.

Profile table 840 is a data structure which identifies what patient information should be transmitted to one or more recipients (or classes of recipients). In accordance with this disclosure, profile table 840 may be structured as one or more tables for each of one or more recipients, or profile table 840 may be structured as one or more tables for one or more classes of recipients. For the purpose of this disclosure, the terms "recipients" and "classes of recipients" should be taken as interchangeable unless the context dictates otherwise. In either instance, profile table 840 includes information that identifies at least one recipient and the types of patient information that such recipient should receive.

For example, certain recipients (e.g., medical personnel) may be identified as receiving all (or substantially all) patient information surrounding a medical event. Other recipients (e.g., family members) may be identified as receiving only a summary of or other notification that a medical event has occurred. Still other recipients (e.g., EMS personnel) may be identified as receiving a different subset of patient information. Yet other recipients (e.g., technical support personnel) may be identifies as receiving still another subset of patient information, which may include more system maintenance information that would be unhelpful to either medical personnel or family members. In various embodiments, different predetermined or even arbitrary categories of recipients may be identified and associated with various profiles. In this way, indirection may be incorporated into embodiments to allow for greater flexibility when associating notifiable events with intended recipients or categories of recipients.

It will be appreciated that the profile table 840 may identify specific patient information or it may identify categories of patient information that should be transmitted to particular recipients. The profile table 840 may further include contact information for each recipient in the profile table 840 to enable the corresponding recipients to receive notifications.

In operation, the event table 820 and the profile table 840 may be used in conjunction to identify which specific patient information should be delivered to which particular recipients based on various notifiable events that may occur. In other words, if a specific notifiable event occurs, the event table 820 may be queried to identify what specific patient information should be reported for that notifiable event. In addition, the profile table 840 may be queried to identify which specific recipients should be notified either based on the particular notifiable event that has occurred, or based on the type of patient information that has been implicated by the notifiable event. In either instance, the profile table 840 identifies which recipients should receive what patient information as a result of the occurrence of the notifiable event.

It should be appreciated that the notification tables 801 have been illustrated as being co-resident for purpose of discussion only. The notification tables 801 may, in various embodiments, be implemented as one or more tables or simply as distributed information that is used collectively to implement the spirit of this disclosure. For example, in certain implementations, all patient information may be transmitted to all subscribed recipients for all notifiable events. In such a case, an app resident on the recipient's receiving device may parse the received patient information and render or display only such patient information as is consistent with the recipient's profile, which profile may be stored on the recipient's receiving device. In such an implementation, there would be no actual "table" as such. Rather, the patient information would simply be displayed in accordance with information recorded in the equivalent of a profile table 840 resident on each particular recipient's receiving device. These and many other alternatives will become apparent to those skilled in the art upon a thorough review of the teachings of this disclosure.

Returning to FIG. 3, notification module 378, in some embodiments, is configured to obtain event information, patient identification information, patient location information, and recipient contact information in response to a determination that one or more recipients should be notified. In some embodiments, the event information (for example, Shock Delivered, VF Detected, VT Detected, Bradycardia Detected and/or Asystole Detected) and the patient identification information is obtained from memory 338 and/or one or more modules of processor 330 such as, for example, modules 232, 234, and 236 (previously described in conjunction with FIG. 2). Notification module 378 in some embodiments is configured to obtain patient location information from location module 386. In some embodiments, the recipient contact information can be entered by the user or clinician when the patient is fitted with the WCD system and updated as desired. The recipients can be people who might be expected to be near patient 182 for significant periods of time such as, for example, spouse, relatives, neighbors, co-workers, assistants, etc. so that assistance can be quickly provided to patient 182.

In a further refinement, after a notification is sent in response to the occurrence of a notifiable event, notification module 378 may be configured to cause the notification to be periodically resent (e.g., every 60 seconds). In some embodiments, the resending of notifications may be terminated in response to one or more recipients sending a message to the WCD system (or, perhaps, an affiliated accessory) that the recipient(s) are in the process of responding to the notification. Alternatively, the notification itself could include a component (e.g., a read receipt, beacon, tracking pixel, or the like) to automatically return an indication that the notification has been received and, perhaps, read.

In some embodiments, WCD system 301 includes a proximity detector (not shown) such as, for example, disclosed in U.S. Pat. No. 9,339,663 issued May 17, 2016 and entitled "WEARABLE CARDIAC DEFIBRILLATOR SYSTEM EMITTING CPR PROMPTS", incorporated by reference herein in its entirety. The proximity detector can be used to detect when bystanders are near the patient. Responsive to the proximity detector detecting such a bystander, in some embodiments, notification module 378 is configured to make a determination that a notification need not be sent to potential recipients. Conversely, responsive to the proximity detector detecting that there are no nearby bystanders, in some embodiments notification module 378 will make a determination that a notification should be sent to recipients.

In still other embodiments, when the aforementioned proximity detector detects nearby bystanders, notification module 378 may be configured to make a determination that a notification should not be sent to recipients. However, in addition, if after a preset period of time (e.g., 30 seconds) the WCD system does not detect CPR has been started on the patient, notification module 378 may be further configured to change the determination so that a notification should be sent to the recipients. In some embodiments, the WCD system may detect CPR by detecting changes in the patient's transthoracic impedance.

Communication module 390, in some embodiments, is configured to transmit at least some of the information obtained by the notification module to one or more respondents using the recipient contact information. In some embodiments, communication module 390 is implemented using a wireless transceiver such as, for example, cellular voice, cellular data, SMS, "Wi-Fi", "Wi-Fi Direct", "Bluetooth", "ZigBee", etc. In some embodiments, these wireless connections may be used to communicate via a server that is configured to initiate communications to the one or more recipients using SMS, email, voice (cellular and POTS), client application notifications (e.g., client apps configured on respondents' computing devices such as smartphones), etc. to the one or more recipients. Various embodiments of these communications are described below in conjunction with FIGS. 4-8.

The above-described embodiments of a WCD system can be advantageously used to provide notifications to various remote recipients based, at least in part, on the particular recipients' desire for and/or ability to make use of the particular patient information based on the type of event experienced. For example, if the patient experienced an arrhythmia that required a shock to correct, a WCD system that included embodiments of external defibrillator 301 (FIG. 3) could notify one class of recipients associated with a medical professional profile and another class of recipients associated with a family members profile. The recipients associated with the medical professional profile may be trained medical personnel, such as the patient's doctor. The patient information delivered to first responders, such as a paramedic, may include information indicating the patient's location so that the recipient(s) can go as quickly as possible to the patient and provide additional assistance such as CPR.

Figure 4:
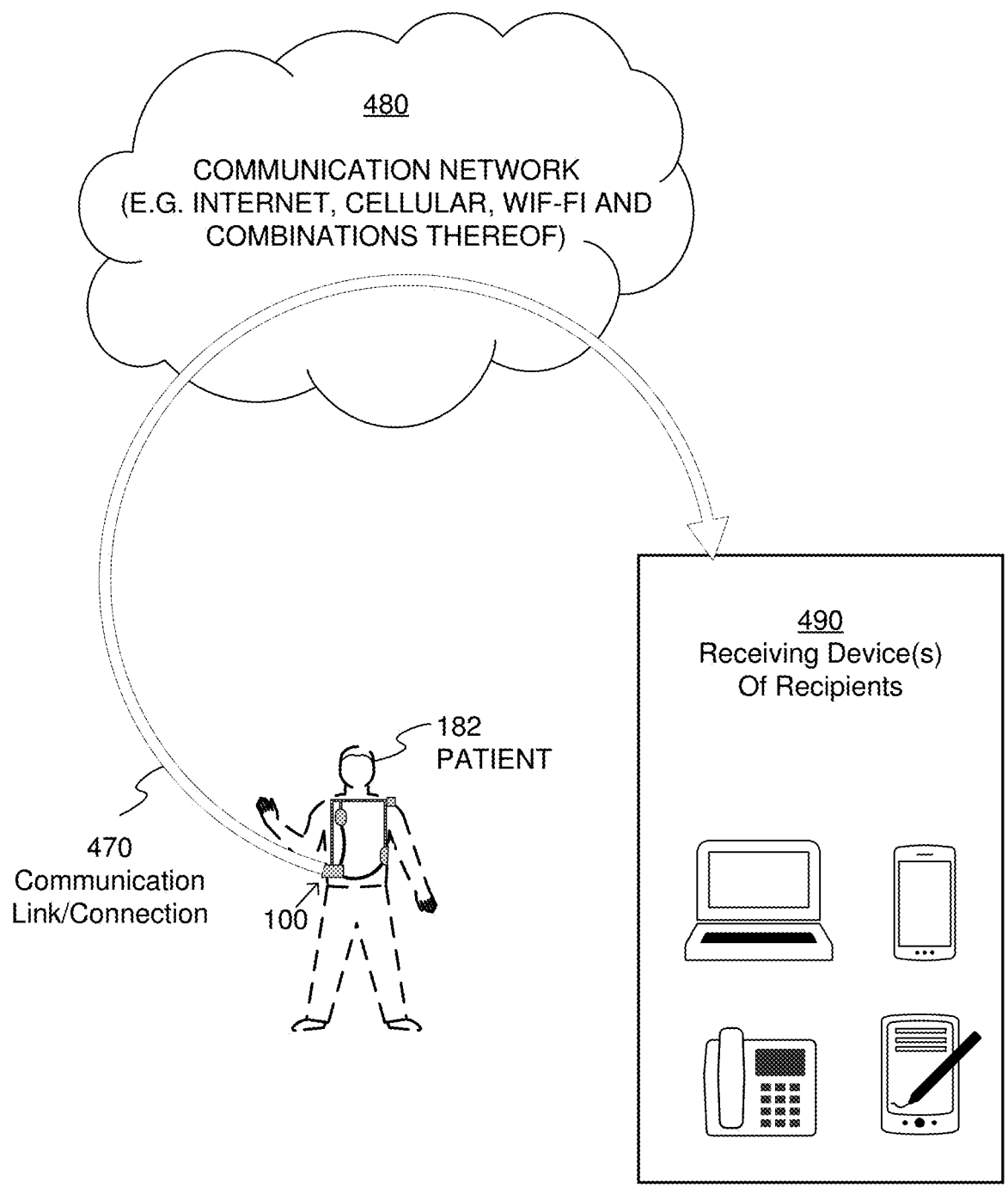
FIG. 4 is a diagram showing a general communication arrangement for a WCD system for issuing notifications to various interested groups by profile, made according to embodiments.

FIG. 4 is a conceptual diagram showing a general communication arrangement for a WCD system for notifying remote recipients, made according to embodiments. FIG. 4 illustrates a general flow of a notification of some notifiable event from the WCD system (e.g., from patient worn external defibrillator 100 described in conjunction with FIG. 1), over a communication link/connection 470 to each of one or more remote recipients via a communication network 480. Each remote recipient may receive a respective notification using the remote recipients' receiving devices 490. Communication network 480 is implemented according to various embodiments using a combination of wireless and/or wired sub links that can include Bluetooth connections, WLAN networks (e.g., Wi-Fi networks), the Internet, POTS, cellular voice networks, cellular data networks, and/or other communication networks. The respondents' devices 490 can include, according to embodiments, computers connected to the communication network 480, cellular telephones, landline telephones, pagers, PDAs, tablet computing devices, and/or smartphones configured with notification applications, etc.

Figure 5:
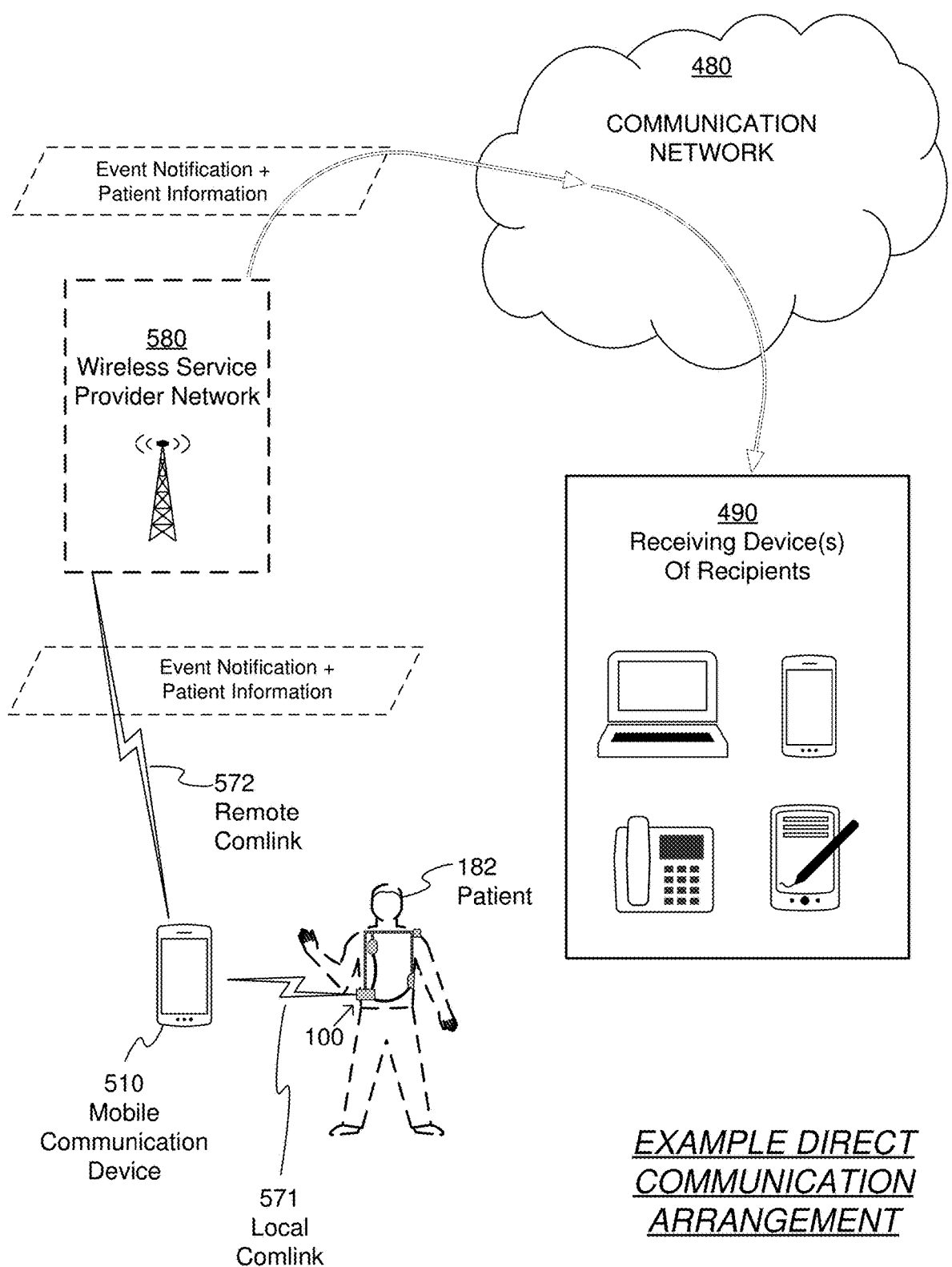
FIG. 5 is a diagram showing a communication arrangement for a WCD system having a mobile communication device for notifying remote responders, made according to embodiments.

FIG. 5 is a diagram showing an embodiment of a particular communication arrangement implementing the general arrangement shown in FIG. 4. The arrangement of FIG. 5, in this embodiment, includes a mobile communication device 510 configured to communicate with external defibrillator 100 through a local commlink 571. In some embodiments, mobile communication device 510 and local commlink 571 may be implemented as described in U.S. patent application Ser. No. 13/959,894 filed Aug. 6, 2013 and entitled "MOBILE COMMUNICATION DEVICE & APP FOR WEARABLE DEFIBRILLATOR SYSTEM". In embodiments, mobile communication device 510 can be a wireless telephone, a smartphone, a Personal Digital Assistant (PDA), a personal electronic device, a pager, a laptop computer, a tablet, an e-reader, and so on. Such mobile communication devices are increasingly becoming more than just wireless voice communication devices. In addition to handling voice data, many mobile communication devices are essentially portable computing devices that can support a variety of applications such as email, instant messaging, web browsing, text processing applications, contact applications, scheduling applications, games, and so on.

In other embodiments, the functionality of mobile communication device 510 may be incorporated directly into the external defibrillator 100. In such a case, no local comlink 571 is necessary as any communication between the functionality of the external defibrillator 100 and the functionality described in conjunction with the mobile communication device 510 would occur intra-device without need for an external communication channel. Mobile communication device 510 is illustrated and described as a separate component for clarity and completeness of discussion only.

In many cases, mobile communication device 510 acts as a proxy for the patient 182. Patient 182 may carry device 510 in a pocket, in a special holder, attached to a garment, on the patient's wrist or belt, or the like. In other words, the location of patient 182 can sometimes be presumed to be the same as the location of mobile communication device 510. In such embodiments, mobile communication device 510 includes a location module that has location determining circuitry and/or software for determining the location of the mobile communication device using GPS, cell tower locations, Wi-Fi access point locations, inertial navigation, etc., as may be available in various smartphones.

The arrangement of FIG. 5 typically uses one or more wireless communication links. A communication link is also sometimes referred to herein as a "comlink". For purposes of this document, a "remote comlink" means a communication link established between devices that are typically about 500 feet (150 m) away from each other, and often farther, such as a cellular communication link. A "local comlink" as used in this context means a communication link established directly between devices that are less than about 500 feet (150 m) away from each other, and typically much closer. A commlink may be either wireless, wired, or some combination of wireless and wired communication links.

In embodiments, mobile communication device 510 can communicate with a wireless service provider network 580 via a remote comlink 572. Remote comlink 572 can be direct, or can be established between device 510 and network 580 via intermediary points, such as a Wireless Access Point, Wi-Fi, and so on; even in those cases, however, a remote comlink includes at least one leg of communication link that is at least 500 feet (150 m) long. One or more of the legs between intermediary points may include a network land line. Network 580 can be coupled with a communications network 480, which can be any wide area network, such as the Internet, POTS, etc. Receiving devices 490 of the recipients can be part of network 480, and in effect be cloud-based. Receiving devices 490, in embodiments, may be any one of a landline telephone, a cellular telephone, a desktop computer, a server, a mainframe computer, and so on. Accordingly, mobile communication device 510 can communicate and exchange data directly with receiving devices 490 of remote recipients, at least according to the arrangement of FIG. 5.

In some embodiments, mobile communication device 510 and/or receiving devices 490 includes an application, also known as an "app" that facilitate the users of these devices in sending and receiving communications, including notifications.

In many embodiments, external defibrillator 100 and mobile communication device 510 are capable of establishing local comlink 571, and therefore can exchange data between them via the local comlink. Data can be exchanged in either direction, or in both directions. In some embodiments, local comlink 571 uses radio transmission technology that can be broadband and/or shortwave. Local comlink 571 may use Bluetooth technology, Wi-Fi technology, or other wireless technology. Local comlink 571, coupled with the abilities of mobile communication device 510, enables external defibrillator 100 to communicate better with its environment.

In other embodiments, instead of wireless comlink 571, defibrillator 100 and mobile communication device 510 may be capable of establishing a comlink that is wired, and therefore can exchange data between them via the wired local comlink. The wired comlink can be by any suitable wired connection, for example via a USB or Lightning connection. Communication could be established by the connecting, whereupon the two devices would recognize each other, and so on.

In operation to provide a notification of notifiable events, in some embodiments, after detection of the event and a determination that notifications should be sent to recipient(s), external defibrillator 100 uses local comlink 571 to provide patient information to the mobile communication device 510. In many embodiments, external defibrillator 100 also provides patient location information to the mobile communication device 510. In other embodiments, mobile communication device 510 determines the patient location information based on location identification functionality (e.g., GPS, Wi-Fi Positioning System (WPS), or the like) built into the mobile communication device 510. In some embodiments, external defibrillator 100 may be configured to send the patient information to mobile communication device 510 before or concurrently with the determination that notifications should be sent to recipient(s).

In accordance with the disclosure, the mobile communication device 510 references notification tables (e.g., Notification Tables 801) to identify which patient information should be shared with each class of recipients that has been registered to receive notifications based on profiles set up for those recipients. In certain embodiments, notifiable events may have particular subsets of patient information that are shared with different recipient profiles. In one example, a first class of recipients (such as medical personnel, Profile "A") may receive all or substantially all of the patient information available. In accordance with the disclosure, the recipients associated with Profile A are chosen or identified as having sufficient training and knowledge that those recipients should be provided with as much patient information about the event as possible to assist those recipients to provide care, and possibly urgent assistance, to the patient.

In contrast, a second class of recipients (such as family or friends, Profile "B") may receive only a subset (or, perhaps, a summary) of the patient information available. In accordance with the disclosure, the recipients associated with Profile B are chosen or identified as having an interest in the patient (such as a familial or other non-medical interest) but they are not necessarily medical professionals and are not in need of detailed medical data (e.g., the patient's ECG trace, or the like) about the event as such information is likely to be confusing and frustrating to those recipients. However, the recipients associated with Profile B may benefit from non-medical patient information (e.g., the patient's location, maintenance data about the WCD system, and the like).

Still further, a third class of recipients (such as EMS personnel, Profile "C") may receive a different subset of the patient information. In accordance with the disclosure, the recipients associated with Profile C may be chosen or identified as having a medical interest in the patient (such as being first responders or other aid-rendering personnel) that differs at least slightly from other classes of recipients. In such a case, the Profile C recipients may benefit from some, but not all, medical data from the patient information (such as the type of event that is occurring, the patient's vital signs and, possibly, ECG data) as well as the patient's location.

Mobile communication device 510 uses remote link 572 to deliver, as appropriate, the pertinent patient information related to the notifiable event, which may include the patient's location, over wireless service provider network 580. In accordance with the embodiment illustrated in FIG. 5, mobile communication device 510 typically uses recipient contact information stored in its memory to direct information to the devices 490 of recipients. In other embodiments, mobile communication device 510 obtains the contact information from external defibrillator 100. In some embodiments, the notification transmitted by the mobile communication network includes information processed and/or revised from the event information obtained from external defibrillator 100 to comply with patient privacy regulations and to provide only what is needed by the potential recipients to be able to quickly travel to the patient and provided assistance such as, for example, CPR.

Wireless service provider network 580, in some embodiments, uses communication network 480 to provide the notification to the receiving device(s) 490 of the recipients.

Figure 6:
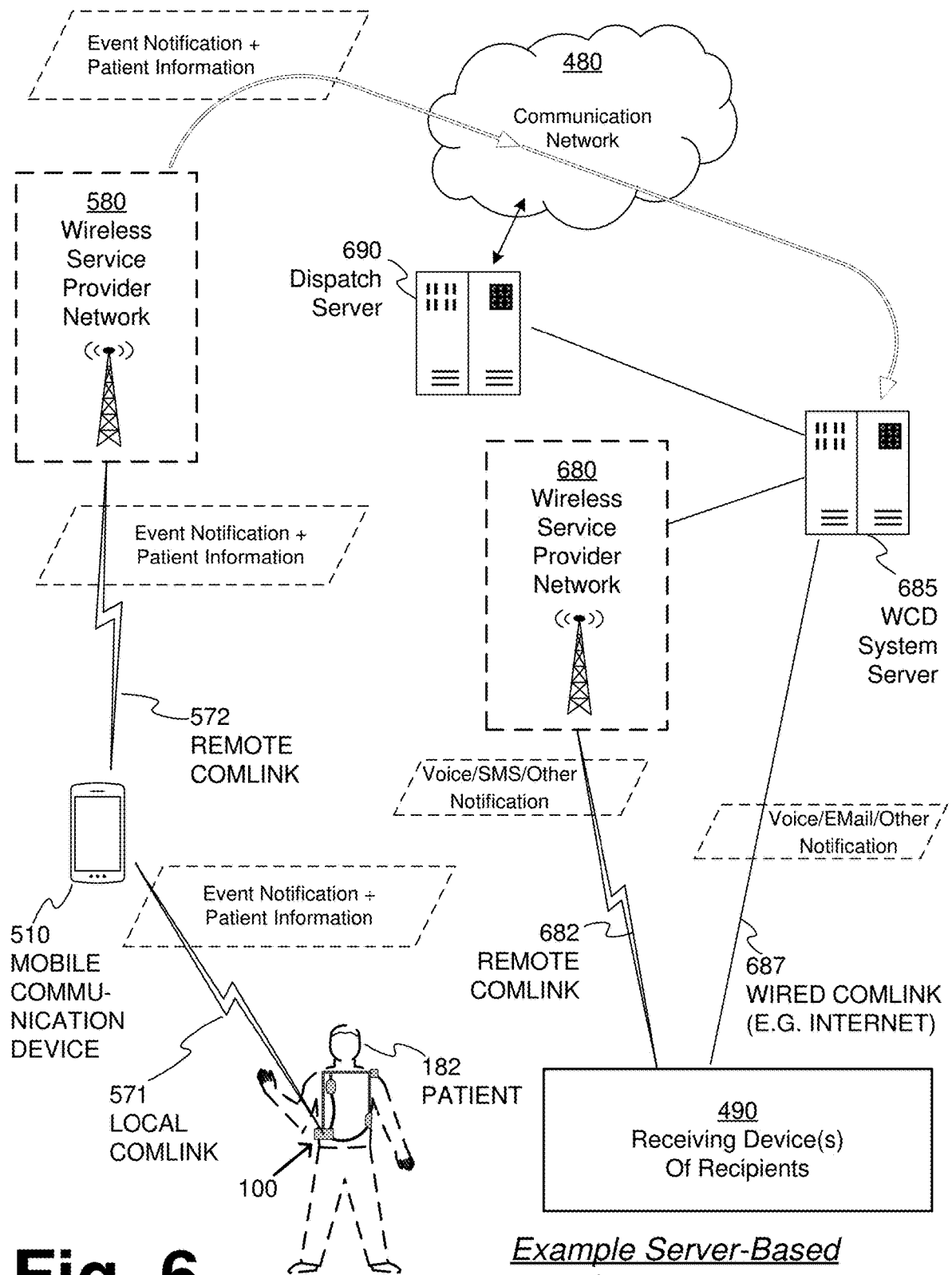
FIG. 6 is a diagram showing a communication arrangement for a WCD system having a WCD system server for notifying remote recipients, made according to embodiments.

FIG. 6 is a diagram showing an embodiment of one particular communication arrangement implementing the general arrangement shown in FIG. 4. The arrangement of FIG. 6, in this embodiment, is similar to the arrangement of FIG. 5 but also includes a WCD server 685 configured to communicate with receiving device(s) 490 through a wireless service provider network 680 via a remote comlink 682 and/or a wired commlink 687. These additional elements may be considered a part of communication network 480 but are "broken out" in FIG. 6 to facilitate this description.

In some embodiments of the arrangement of FIG. 6, mobile communication device 510 receives patient information from external defibrillator 100 via local commlink 571, sends notification information to wireless service provider network 580, which then sends notification information to communication network 480, all as described above in conjunction with FIG. 5.

For such embodiments, the notification information sent by mobile communication device 510 may also include information addressing the notification to WCD server 685. In some embodiments, notification tables (e.g., notification tables 801) may be stored in WCD server 685 and the WCD server 685 is configured to access recipient contact information based on the notifiable event and/or patient information. In such embodiments, such recipient contact information may be stored in one or more notification tables that identify one or more recipient profiles, as discussed in detail above. In such embodiments, and as discussed above, different recipients or classes of recipients may be identified to receive different sets or subsets of patient information.

WCD server 685 processes notification information received via communication network 480 to generate one or more notification messages. For example, in some embodiments, WCD server 685 is configured with profile and preference information for each recipient and generates the appropriate notification message for that recipient (and/or the recipient's device 490). For receiving devices 490 that are wireless (e.g., cell phones, smartphones, connected tablets, connected laptops, pagers, etc.), WCD system server 685 in some embodiments generates one or more SMS messages, recorded/synthesized voice messages, emails, or the like to be sent to those devices via a wireless service provider network 680 and a remote comlink 682. Similarly, for receiving devices 490 that are wired or potentially wired (e.g., a landline telephone, a desktop computer, etc.), WCD system server 685 in some embodiments generates one or more email messages, recorded or synthesized voice messages, or the like to be sent to those devices via a wired comlink 687 such as the Internet, POTS, etc. The particular type of notification message for each receiving device 490 may be selected by WCD system server 685 based on contact information, emergency event and/or stored profile/preference information.

In certain embodiments, one or more recipients may include a Dispatch Server 690 (e.g., a computer-aided dispatch (CAD)-coupled server), such as may be employed by an EMS or first responder service. In such an embodiment, one or more receiving devices 490 may include apps for use with Dispatch Server 690.

In a typical operation, Dispatch Server 690 would receive notification of certain types of notifiable events (e.g., cardiac arrest and the patient's reported location) from the WCD System Server 685 and, in response, send an alert (e.g., "CPR needed") to subscribers' devices that are near the patient's reported location.

For example, in embodiments where one or more recipients have been identified with a profile indicating that those one or more recipients may be first responders or other EMS personnel, the WCD system server 685 may be configured to communicate either directly with the Dispatch Server 690 over a direct communication link, or perhaps over the general-purpose wide area communication network 480. In such embodiments, an appropriate subset of patient information (including the location of the patient 182) may be forwarded immediately to the Dispatch Server 690 for prompt action, such as dispatching emergency responders.

Further, in some embodiments, in response to received notifications, a recipient can use his/her receiving device 490 to send a message to WCD server system 685 indicating that the recipient is going to respond to provide the additional assistance, or cannot respond, etc. Still further, in some such embodiments, the WCD system server can then send notifications to other recipients indicating the recipient(s) who have indicated that they were are responding to provide the additional assistance. For example, the WCD system service can send these notifications to other recipients via SMS message, or in direct application communication (described below).

Figure 7:
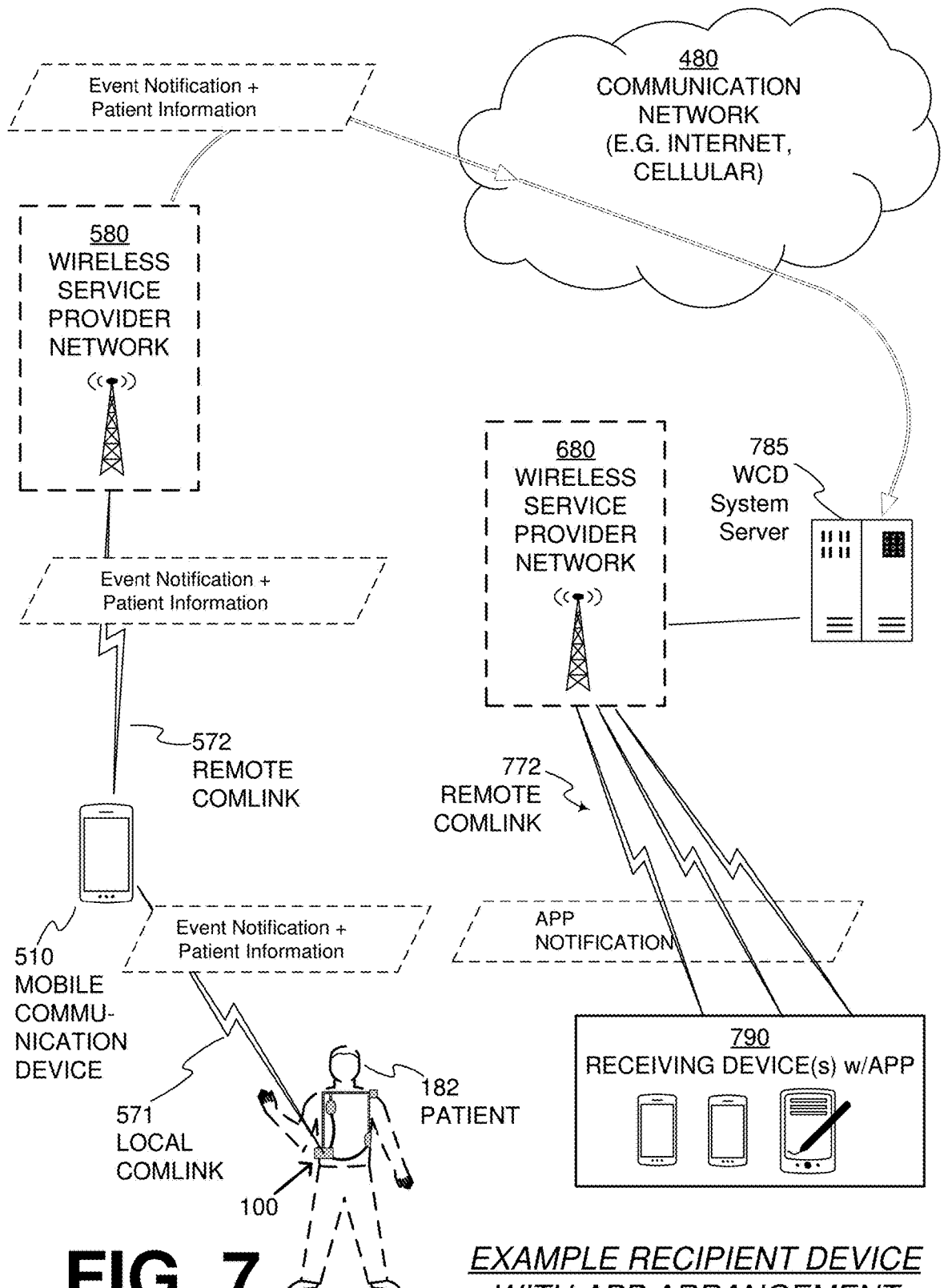
FIG. 7 is a diagram showing a communication arrangement for a WCD system for notifying remote recipients having devices configured with a notification app, made according to embodiments.

FIG. 7 is a diagram showing another embodiment of a particular communication arrangement implementing the general arrangement shown in FIG. 4. The arrangement of FIG. 7, in this embodiment, is similar to the arrangements of FIG. 5 or FIG. 6 but also includes receiving devices 790 of non-witness responders (e.g., a socially distanced CPR coach or other medical personnel guiding a direct care provider) or other remote recipients having a notification app installed for receiving notifications from a WCD system server 785. WCD system server 785, in some embodiments has the same functionality as WCD system server 685 (FIG. 6) but in addition is configured to send notifications to the receiving devices 790.

In some embodiments, WCD system server 785 and the apps installed on receiving devices 790 implement an event subscription architecture. For example, in some embodiments when WCD server 785 receives a notification of a notifiable event via communication 480, this generates an event action in the WCD system server 785. In response, WCD system server 785 publishes the notifiable event to subscribed clients (i.e., the apps installed on receiving devices 790) via wireless service provider network 680 and remote commlink 772. In such an embodiment, each subscribed client may have an associated profile that identifies a set or subset of patient information to be transmitted to such subscribed client. In other embodiments, other messaging mechanisms can be used instead of or in combination with an event subscription architecture, such as for example SMS text, Apple iMessage, or other network messaging systems. In response to receiving the published event, the apps on receiving devices 790 then provide an alarm or alert via the user interface of the receiving devices. In some embodiments, the app is configured to provide the alert using audio, visual and/or vibration outputs of the receiving device.

The various embodiments of the devices and/or systems disclosed in this document perform functions, processes and/or methods as described above. These functions, processes and/or methods may be implemented by one or more devices that include logic circuitry. Such a device can be alternately called a computer, and so on. It may be a standalone device or computer, such as a general-purpose computer, or part of a device that has one or more additional functions. In some embodiments, the computer is a specialized computer adapted to and optimally configured for a specific purpose such as for example, providing therapy shocks in emergency situations. The logic circuitry may include a processor and non-transitory computer-readable storage media, such as memories, of the type described in this document. Often, for the sake of convenience, it is preferred to implement and describe a program as various interconnected distinct software modules or features. These, along with data are individually and also collectively referred to herein as software. In some instances, software is combined with hardware, in a mix called firmware.

Various embodiments of methods and algorithms are described below. These methods and algorithms are not necessarily inherently associated with any particular logic device or other apparatus. Rather, they can be advantageously implemented by programs for use by a computing machine, such as a general-purpose computer, a special purpose computer, a microprocessor, a microcontroller, a processor and/or a combination of these devices such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts describe methods in terms of boxes, they also concurrently describe programs.

Figure 9:
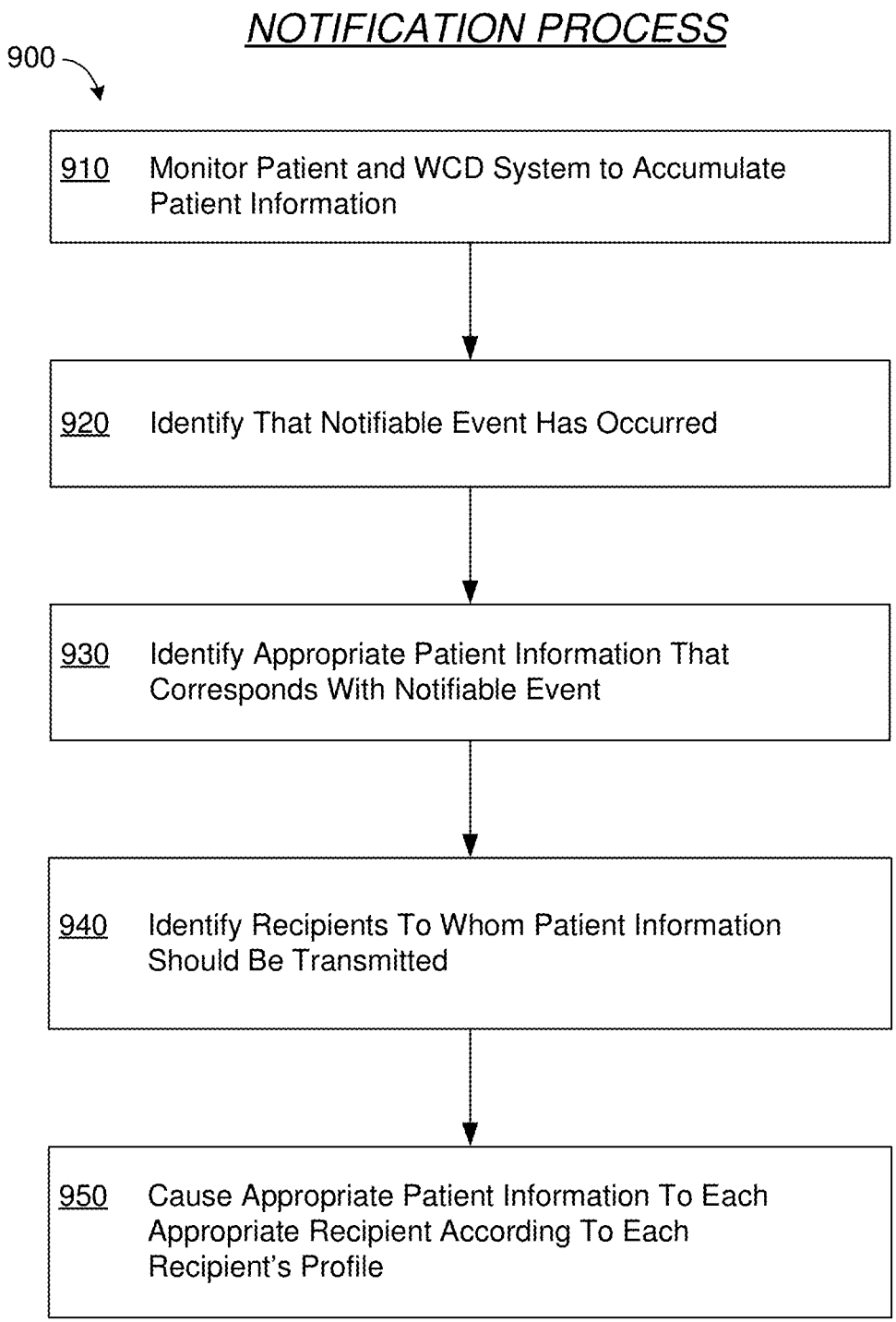
FIG. 9 is a flow diagram illustrating sample methods for use in a WCD system to notify remote responders, according to embodiments.

FIG. 9 is a flow diagram generally illustrating a notification process 900 for use in a WCD system (such as described above in conjunction with FIGS. 2-8) to notify remote recipients of a notifiable event, according to embodiments. Notification process 900, in some embodiments, can start when the WCD system encounters a notifiable event as previously described.

At operation 910, the process 900 monitors a patient, the WCD system itself, and perhaps environmental conditions to accumulate patient information. The patient information may include patient state parameters, system parameters, environmental parameters, and the like.

At operation 920, the process 900 identifies that a notifiable event has occurred. The notifiable event may be any occurrence deemed, by the WCD system programming, to warrant issuing a notification to systems or individuals external to the WCD system. Non-exhaustive examples of notifiable events include medical events pertaining to the health of the patient (e.g., arrythmia, SCA, or the like), events pertaining to the patient's compliance with prescribed wear of the WCD system, maintenance events (e.g., low battery warnings, electrode expiry, other system warnings or the like), manually entered event notifications (e.g., wear-time compliance indicators, geofencing indicators, etc.), and any other occurrence detectable by the WCD system. It should be noted that all "events" detectable by the WCD system need not necessarily constitute a "notifiable event" within the context of this disclosure (although they could).

At operation 930, the process 900 identifies what patient information to transmit based on the type of notifiable event. In certain embodiments, any notifiable event may implicate all patient information accumulated or identified at operation 910. In other embodiments, particular notifiable events may implicate only event-based subsets of the patient information. In this other embodiments, the patient information may be parsed At operation 940, the process 900 identifies recipients to whom patient information should be transmitted. As noted above, different recipients may be in disparate positions regarding what patient information is appropriate or proper to transmit to them. For example, medical personnel may be in a position to better understand and act upon more patient information than lay persons for many notifiable events, such as medical events. In contrast, other recipients, even non-medical personnel, may be in a position to better act upon other notifiable events, such as a maintenance condition with the WCD system (e.g., a low battery condition). Accordingly, the process 900 may refer to recipient profiles to identify appropriate patient information to transmit to each subscribed potential recipient.

At operation 950, the process 900 causes notification information to be transmitted to each appropriate recipient based on the appropriate patient information for the notifiable event and the appropriate patient information for the particular recipients. In various embodiments, the process 900 may cause the WCD system to transmit the appropriate notification (populated with the appropriate patient information) directly to each recipient. In other embodiments, the process 900 may cause a WCD system server to transmit the appropriate notifications. In still other embodiments, the process 900 may perform some combination of transmitting notifications directly from the WCD system and transmitting notifications using a WCD system server.

In various implementations, the notifications may take any one or more of various forms. For instance, notifications may take the form of pre-recording audible messages. Alternatively, notifications may take the form of electronic messages assembled using the appropriate patient information and delivered via electronic means. In yet another alternative, notifications may be transmitted using a cellular SMS system. In still another alternative, notifications my be transmitted as electronic communications between a host and client each operating special purpose programmed applications. In various combinations and implementations, combinations of one or more of the foregoing protocols may be employed, even in combination with other communication protocols.

In various other implementations, at least some of the patient information received by the WCD system server is transmitted by the WCD system server to a CAD-coupled server such as, for example, Dispatch Server as described above in conjunction with FIG. 7. In some embodiments, the Dispatch Server may be enhanced to receive/process information from the WCD system server, and the information transmitted may not include contact information for potential responders as the Dispatch Server could have this information.

In the methods described above, each operation can be performed as an affirmative step of doing, or causing to happen, what is written that can take place. Such doing or causing to happen can be by the entire system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily the present invention. Plus, any reference to any prior art in this description is not, and should not be taken as, an acknowledgement or any form of suggestion that this prior art forms parts of the common general knowledge in any country.

This description includes one or more examples, but that does not limit how the invention may be practiced. Indeed, examples or embodiments of the invention may be practiced according to what is described, or yet differently, and also in conjunction with other present or future technologies. Other embodiments include combinations and sub-combinations of features described herein, including for example, embodiments that are equivalent to: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, a phrase in the form of "A and/or B" is used to indicate "A or B or both A and B". Further, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in any number of ways, as will be apparent to a person skilled in the art after reviewing the present disclosure, beyond any examples shown in this document.

The following claims define certain combinations and subcombinations of elements, features and steps or operations, which are regarded as novel and non-obvious. Additional claims for other such combinations and subcombinations may be presented in this or a related document.

What is claimed is:

1. A wearable cardioverter defibrillator (WCD) system, comprising: a support structure configured to be worn by a patient;
a plurality of electrodes coupled to or integrated in the support structure;
an energy storage module;
a discharge circuit configured to be coupled to the energy storage module and configured to deliver one or more shocks to the patient while the support structure is worn by the patient using the plurality of electrodes and electrical charge stored in the energy storage module; and
at least one processor comprising:
a location module configured to determine a location of a component of the WCD system;
an event detection module configured to detect an occurrence of a notifiable event;
a notification table that includes information used to identify a first subset of patient information to transmit to a first recipient and to identify a second subset of patient information to transmit to a second recipient;
one or more profile tables identifying the first recipient and the second recipient;
a notification module coupled to the event detection module, the notification module being configured to identify patient information that is implicated by the notifiable event, and to identify the first subset of the patient information to transmit to the first recipient and the second subset of the patient information to transmit to the second recipient; and
a communication module, coupled to the notification module, configured to transmit the first subset of patient information to the first recipient and to transmit the second subset of patient information to the second recipient,
wherein the first subset of patient information and the second subset of patient information include a tracking component, configured to automatically output an indication that the notification has been received, read, or a combination thereof.

2. The WCD system of claim 1, further comprising:
a WCD system server that includes information used to identify the first subset of patient information to transmit to the first recipient and to identify the second subset of patient information to transmit to the second recipient.

3. The WCD system of claim 1, further comprising a mobile communication device configured to be coupled to the at least one processor and to implement at least a part of the communication module.

4. The WCD system of claim 3, in which the mobile communication device further implements the location module.

5. The WCD system of claim 1, in which the first subset and the second subset of the patient information are identified in the one or more profile tables.

6. The WCD system of claim 1, in which the one or more profile tables include(s) information that associates particular subsets of patient information with subscribed recipients, at least two subscribed recipients have different corresponding subsets of patient information.

7. The WCD system of claim 6, in which the communication module is configured to transmit the patient information and a notification of the notifiable event to a WCD system server and the WCD system server implements the notification module and the profile tables to facilitate the transmission of the first subset of the patient information to the first recipient and the second subset of the patient information to the second recipient.

8. The WCD system of claim 7, in which the first recipient comprises a dispatch server and the WCD system server is further configured to communicate at least the first subset of patient information to the dispatch server, the dispatch server being configured to communicate at least a portion of the transmitted information from the WCD system server to one or more responders.

9. The WCD system of claim 2, wherein the notification table is hosted on a remote server accessible using the communication module.

10. The WCD system of claim 1, wherein the patient information comprises the location of the support structure.

11. A method for use in a wearable cardioverter defibrillator (WCD) system comprising a support structure configured to be worn by a patient, and a plurality of electrodes coupled to or integrated in the support structure, the method comprising:
monitoring by at least one processor of the WCD system one or more parameters comprising at least one physiological parameter or system parameter collectively referred to as patient information;
determining by the WCD system a location of the patient;
determining by the WCD system that a notifiable event has occurred, the notifiable event implicating at least one of the one or more parameters;
responsive to a determination by the WCD system that the notifiable event has occurred, identifying a first recipient and a second recipient, and further identifying a first subset of the patient information associated with the first recipient and a second subset of the patient information associated with the second recipient, wherein identifying the first and second recipients comprises querying a notification table that associates profile information with a plurality of recipients, the first and second recipients being within the plurality of recipients;
querying one or more profile tables identifying the first recipients and the second recipients and provided contact information for transmitting the first subset of patient information and the second subset of patient information, respectively;
initiating, by the WCD system, a transmission of the first subset of the patient information to the first recipient and a transmission of the second subset of the patient information to the second recipient, wherein the transmission of the first subset of the patient information to the first recipient and the transmission of the second subset of the patient information to the second recipient each include a tracking component, configured to automatically output an indication that the notification has been received, read, or a combination thereof.

12. The method recited in claim 11, wherein the one or more parameters comprise one or more physiological parameters of the patient while the patient is wearing the support structure, and one or more system parameters of the WCD system that reflect a status of the WCD system.

13. The method of claim 11, further comprising determining by the WCD system a location of a component of the WCD system, and wherein the first and second subsets of the patient information further include the location of the component of the WCD system.

14. The method of claim 13, wherein the WCD further comprises a mobile communication device separate from the at least one processor, wherein the mobile communication device is used at least in part in determining the location of the component of the WCD system, and wherein the mobile communication device assists with the transmission of the first and second subsets of the patient information.

15. The method of claim 14, wherein a WCD system server queries the notification table that associates profile information with a plurality of recipients, the first and second recipients being within the plurality of recipients.

16. The method of claim 11, wherein the first subset of patient information is different, at least in part, from the second subset of patient information.

17. The method of claim 11, wherein the notifiable event comprises at least one of a medical event associated with the patient or a maintenance event associated with the WCD system.

18. The method of claim 11, wherein identifying the first and second recipients is performed by a remote WCD system server, and wherein the WCD system server participates in the transmission of the first subset and the second subset of patient information.

19. The method of claim 18, wherein the WCD system server transmits the first subset of patient information to a dispatch server with which the first recipient is associated, the dispatch server being configured to dispatch one or more responders to the location of the WCD system.

20. The WCD system of claim 11, wherein the transmission includes an indication that the patient requires cardiopulmonary resuscitation (CPR).

21. The method of claim 11, wherein the notifiable event further comprises an indication of a desire to transmit a broadcast message, and wherein identifying the first recipient and the second recipient comprises identifying any potential recipients that are registered to receive broadcast messages.

22. The WCD system of claim 1, wherein at least one WCD accessory is configured to passively collect patient activity information, wherein the patient activity information is used by the event detection module to detect the occurrence of the notifiable event.

\* \* \* \* \*